(12) United States Patent
Bratt et al.

(10) Patent No.: US 7,419,979 B2
(45) Date of Patent: Sep. 2, 2008

(54) DERIVATIVES OF 6-{4-[4-(1H-INDOLE-2-SULPHONYL)-PIPERAZIN-1-CARBONYL-PHENYL]}PYRADIZIN-3-ONE

(75) Inventors: Emma Bratt, Mölndal (SE); Yantao Chen, Mölndal (SE); Kenneth Granberg, Mölndal (SE); Ingemar Nilsson, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/584,473

(22) PCT Filed: Jan. 5, 2005

(86) PCT No.: PCT/SE2005/000011

§ 371 (c)(1),
(2), (4) Date: Jun. 23, 2006

(87) PCT Pub. No.: WO2005/065688

PCT Pub. Date: Jul. 21, 2005

(65) Prior Publication Data

US 2007/0135441 A1    Jun. 14, 2007

(30) Foreign Application Priority Data

Jan. 8, 2004    (SE) .................................... 0400014

(51) Int. Cl.
*C07D 403/12*    (2006.01)
*C07D 403/14*    (2006.01)
*A61K 31/501*    (2006.01)
*A61P 7/02*    (2006.01)

(52) U.S. Cl. .................. 514/252.02; 544/238

(58) Field of Classification Search ................. 544/238; 514/252.02
See application file for complete search history.

(56) References Cited

U.S. PATENT DOCUMENTS 6,395,731 B1    5/2002    Thorsten et al.

FOREIGN PATENT DOCUMENTS

| EP | 1104754 A1 | 6/2001 |
| WO | WO 9957099 A1 | 11/1999 |
| WO | WO 9957113 A1 | 11/1999 |

*Primary Examiner*—Bruck Kifle
(74) *Attorney, Agent, or Firm*—Morgan, Lewis & Bockius LLP

(57) ABSTRACT

The invention relates to heterocyclic derivatives of formula (I), wherein $R^2$ is amino, a group $OR^4$ or a group $—Y—R^5$ where $R^4$ is hydrogen or $C_{1-4}$alkyl, Y is $C_{1-4}$alkylene, $R^5$ is hydrogen, halo, hydroxy, $C_{1-2}$alkoxy, $C_{1-2}$alkoxy$C_{1-2}$alkoxy$C_{1-4}$, or a group $NR^7R^8$ where $R^7$ and $R^8$ are independently selected from hydrogen, $C_{1-2}$alkyl, hydroxy$C_{1-2}$alkyl or alkoxy$C_{1-2}$alkyl, or $R^7$ and $R^8$ together with the nitrogen atom to which they are attached form a saturated 5-6-membered heterocyclic ring which optionally contains an additional heteroatom; n is one or two and each $R^1$ is independently selected from halo, halo$C_{1-2}$alkyl, hydroxy, oxo, amino, $C_{1-2}$alkylamino or di-$C_{1-2}$dialkylamino; or a pharmaceutically acceptable salt thereof. These compounds possess antithrombotic and anticoagulant properties and are accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect.

(I)

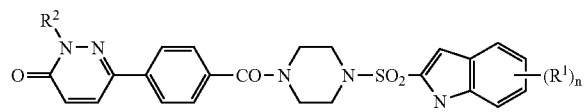

12 Claims, No Drawings

DERIVATIVES OF 6-{4-[4-(1H-INDOLE-2-SULPHONYL)-PIPERAZIN-1-CARBONYL-PHENYL]}PYRADIZIN-3-ONE

The invention relates to heterocyclic derivatives, or pharmaceutically-acceptable salts thereof, which possess antithrombotic and anticoagulant properties and are accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by B.-Y. Zhu, R. M. Scarborough, *Current Opinion in Cadiovascular, Pulmonary & Renal Investigational Drugs,* 1999, 1(1), 63-88. Thus it is known that two proteins, one known as recombinant antistasin (r-ATS) and the other known as recombinant tick anticoagulant protein (r-TAP), are specific direct Factor Xa inhibitors which possess antithrombotic properties in various animal models of thrombotic disease.

It is also known that certain non-peptidic compounds possess Factor Xa inhibitory properties. Of the low molecular weight inhibitors mentioned in the review by B.-Y. Zhu and R. M. Scarborough, many inhibitors possess a strongly basic group such as an amidinophenyl or amidinonaphthyl group.

We have now found that certain heterocyclic derivatives possess Factor Xa inhibitory activity. Many of the compounds of the present invention also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

The compounds of the present invention possess activity in the treatment or prevention of a variety of medical disorders where anticoagulant therapy is indicated, for example in the treatment or prevention of thrombotic conditions such as coronary artery and cerebro-vascular disease. Further examples of such medical disorders include various cardiovascular and cerebrovascular conditions such as myocardial infarction, the rupture of atherosclerotic plaques, venous or arterial thrombosis, coagulation syndromes, vascular injury including reocclusion and restenosis following angioplasty and coronary artery bypass surgery, thrombus formation after the application of blood vessel operative techniques or after general surgery such as hip replacement surgery, the introduction of artificial heart valves or on the recirculation of blood, cerebral infarction, cerebral thrombosis, stroke, cerebral embolism, pulmonary embolism, ischemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

WO 98/21188 describes a range of Factor Xa inhibitors. Further particular examples of this type of compound including 1-(5-chloroindol-2-ylsulphonyl)-4-[4-(6-oxo-1H-pyridazin-3-yl) benzoyl]piperazine are described in WO 99/57113. The applicants have found however, that by further derivatising the compounds of this type, enhanced properties may be obtained.

The present invention provides a compound of formula (I)

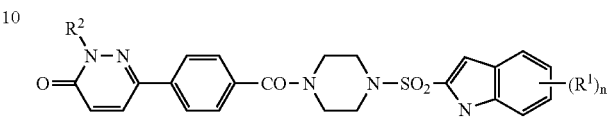

(I)

wherein $R^2$ is amino, a group $OR^4$ or a group —Y—$R^5$ where $R^4$ is hydrogen or $C_{1-4}$alkyl,
Y is $C_{1-4}$alkylene,
$R^5$ is hydrogen, halo, hydroxy, $C_{1-2}$alkoxy, $C_{1-2}$alkoxy$C_{1-2}$alkoxy, or a group $NR^7R^8$ where $R^7$ and $R^8$ are independently selected from hydrogen, $C_{1-2}$alkyl, hydroxy$C_{1-2}$alkyl or alkoxy$C_{1-2}$alkyl, or $R^7$ and $R^8$ together with the nitrogen atom to which they are attached form a saturated 5-6-membered heterocyclic ring which optionally contains an additional heteroatom;
n is one or two and each $R^1$ is independently selected from halo, halo$C_{1-2}$alkyl, hydroxy, oxo, amino, $C_{1-2}$alkylamino or di-$C_{1-2}$dialkylamino;
and pharmaceutically acceptable salts thereof.

In this specification the term "alkyl" includes both straight and branched chain alkyl groups but references to individual alkyl groups such as "propyl" are specific for the straight chain version only. An analogous convention applies to other generic terms.

For the avoidance of doubt, the atoms of the indolyl ring appearing in formula (I) is numbered as drawn below:

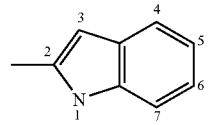

2-indolyl

It is to be understood that certain heterocyclic derivatives of the present invention can exist in solvated as well as unsolvated forms such as, for example, hydrated forms. It is to be understood that the invention encompasses all such solvated forms which possess Factor Xa inhibitory activity.

It is further to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or by resolution of a racemic form.

Compounds of the invention are potent inhibitors of Factor Xa, and may have better solubility and/or less cytochrome P 450 (CYP$_{450}$) inhibition and/or Caco2-permeability than some related compounds. Caco2 is a cell line which mimics transport over the gut wall.

Suitable values R¹ and/or R² are:

for $C_{1-4}$alkyl: methyl, ethyl, propyl, isopropyl and n-butyl, isobutyl;

for halo: fluoro, chloro, bromo;

for $C_{1-4}$alkylamino: methylamino, ethylamino, propylamino;

for di-$C_{1-4}$alkylamino: dimethylamino, diethylamino, N-methyl-N-ethylamino;

for halo$C_{1-4}$alkyl: fluoromethyl, 1-fluoroethyl, 2-fluoroethyl, trifluoromethyl or trifluoroethyl.

for amino$C_{1-4}$alkyl aminomethyl, or aminoethyl, for $C_{1-2}$alkylamino$C_{1-4}$alkyl methylaminomethyl, ethylaminomethyl, ethylaminoethyl, methylaminoethyl, for di-$C_{1-2}$dialkylamino$C_{1-4}$alkyl; dimethylaminomethyl, diethylaminomethyl, diethylaminoethyl, methylethylaminomethyl, methylethylaminoethyl.

for hydroxy$C_{1-4}$alkyl: hydroxymethyl, 1-hydroxyethyl, 2-hydroxyethyl and 3-hydroxypropyl;

for $C_{1-2}$alkoxy$C_{1-4}$alkyl: methoxymethyl, ethoxymethyl, 1-methoxymethyl, 2-methoxyethyl, 2-ethoxyethyl and 3-methoxypropyl;

for $C_{1-4}$alkoxy: methoxy, ethoxy;

In particular, $R^2$ is a group —Y—$R^5$.

Suitably Y is a $C_{1-2}$alkylene group.

Examples of groups $R^5$ are hydrogen, halo, hydroxy, methoxy, methoxy$C_{1-2}$alkoxy, or a group $NR^7R^8$ where $R^7$ and $R^8$ are as defined above.

A preferred group $R^5$ is hydrogen, so that particular examples of $R^2$ are methyl or ethyl. A particularly preferred example of $R^2$ is methyl.

In an alternative embodiment, $R^2$ is a group —Y—$R^5$ where $R^5$ a group $NR^7R^8$ where $R^7$ and $R^8$ are independently selected from hydrogen, $C_{1-2}$alkyl, hydroxy$C_{1-2}$alkyl or alkoxy$C_{1-2}$alkyl, or $R^7$ and $R^8$ together with the nitrogen atom to which they are attached form a saturated 5-6-membered heterocyclic ring which optionally contains an additional heteroatoms. Suitably at least one of $R^7$ or $R^8$ is a hydroxy$C_{1-2}$ alkyl or alkoxy$C_{1-2}$alkyl group, such as methoxyethyl.

In particular, where $R^7$ and $R^8$ together form a saturated heterocyclic ring, it contains a further heteroatom selected from oxygen and sulphur, and in particular oxygen. Particular examples of such groups are morpholino.

Preferably n is 1 or 2, and most preferably, it is 1.

Particular groups $R^1$ are halo groups such as bromo or chloro. Preferably a group $R^1$ is present at a position equivalent to the 5-position as numbered on the indole ring.

Particular compounds of the invention are shown in the following Table.

TABLE

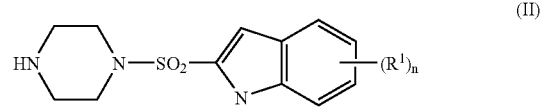

| Compound No. | $R^2$ | $R^{1a}$ | $R^{1b}$ |
|---|---|---|---|
| 1 | $CH_3$ | H | Cl |
| 2 | —$(CH_2)_2N(CH_3)_2$ | H | Cl |
| 3 | —$(CH_2)_2NH(CH_3)$ | H | Cl |
| 4 | —$CH_2CH_3$ | H | Cl |
| 5 | —$(CH_2)_3CH_3$ | H | Cl |
| 6 | —$(CH_2)_2OH$ | H | Cl |
| 7 | —$CH_2CF_3$ | H | Cl |
| 8 | —$(CH_2)_2OCH_3$ | H | Cl |
| 9 | —$(CH_2)_2O(CH_2)_2OCH_3$ | H | Cl |

TABLE-continued

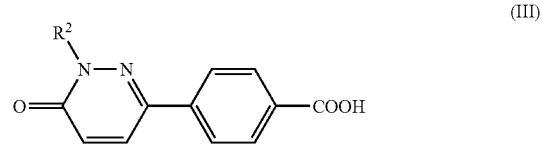

| Compound No. | $R^2$ | $R^{1a}$ | $R^{1b}$ |
|---|---|---|---|
| 10 | —$(CH_2)_2$—N(morpholino) | H | Cl |
| 11 | —$(CH_2)_2NH(CH_2)_2OCH_3$ | H | Cl |

A heterocyclic derivative of formula I, or pharmaceutically-acceptable salt thereof, may be prepared by any process known to be applicable to the preparation of related compounds, such as those described in WO 98/21188 and WO 99/57113. Such procedures are provided as a further feature of the invention and are illustrated by the following representative processes in which, unless otherwise stated any functional group, for example amino, aminoalkyl, carboxy, indolyl or hydroxy, is optionally protected by a protecting group which may be removed when necessary.

Necessary starting materials may be obtained by standard procedures of organic chemistry and by reference to the processes used in the Examples.

For instance, the present invention provides a process for preparing a compound of formula (I) or a pharmaceutically acceptable salt thereof, which comprises the reaction, conveniently in the presence of a suitable base, of an amine of formula (II)

(II)

with an acid of the formula (III)

(III)

wherein $R^2$ is as defined above in relation to formula (I), or a reactive derivative thereof.

A suitable reactive derivative of an acid of the formula (III) is, for example, an acyl halide, for example an acyl chloride formed by the reaction of the acid and an inorganic acid chloride, for example thionyl chloride; a mixed anhydride, for example an anhydride formed by the reaction of the acid with a chloroformate such as isobutyl chloroformate or with an activated amide such as 1,1'-carbonyldiimidazole; an active ester, for example an ester formed by the reaction of the acid and a phenol such as pentafluorophenol, an ester such as pentafluorophenyl trifluoroacetate or an alcohol such as N-hydroxybenzotriazole or N-hydroxysuccinimide; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethyl-carbodiimide.

The reaction is conveniently carried out in the presence of a suitable base such as, for example, an alkali or alkaline earth metal carbonate, also preferably carried out in a suitable inert solvent or diluent, for example methylene chloride, and at a temperature in the range, for example, −78° C. to 150° C., conveniently at or near ambient temperature.

A suitable protecting group for an amino or aminoalkyl group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. An arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

Compounds of formula (III) are suitably prepared by deprotecting a compound of formula (IV)

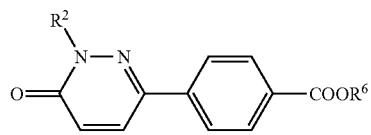

(IV)

where $R^6$ is an acid protecting group such as a $C_{1-6}$alkyl group, and in particular methyl or ethyl. This may be removed using methods described above for the removal of esterifying protecting groups. Alternatively, compounds of formula (III) can be prepared by hydrolysis of a compound of formula (IVA)

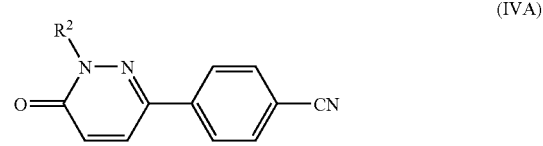

(IVA)

Generally, this reaction is carried out by reacting the compound of formula (IVA) with an acid such as a strong mineral acid, for instance, sulphuric acid, at elevated temperatures, for example from 50° C. to 150° C., and subsequent reaction with a base such as sodium hydroxide, to form the corresponding benzamide. This can then be dissolved in an organic solvent such as an alcohol, such as ethanol, and treated with sodium hydroxide to produce the desired acid. Alternatively the nitrile group is hydrolysed by alkali metal hydroxides in aqueous solutions at temperatures of from 20° C. to 150° C.

Compounds of formula (IVA) can be prepared from compounds of formula (IVB)

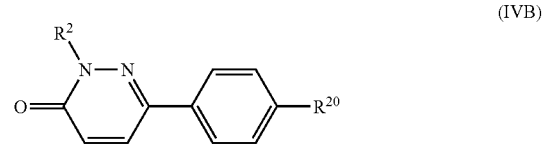

(IVB)

where $R^{20}$ is a halo group by conventional methods. For instance using CuCN in dimethylformamide or 1-methyl-2-pyrrolidinone or by palladium catalysis using e.g. Pd(PPh$_3$)$_4$ and Zn(CN)$_2$ in DMF or Pd(OAc)$_2$, PPh$_3$ and Zn(CN)$_2$ in 1-methyl-2-pyrrolidinone at temperatures of from 0° C. to 150° C.

In an alternative embodiment, the compound of formula (IV) is obtained by alkylation of a compound of formula (IVC)

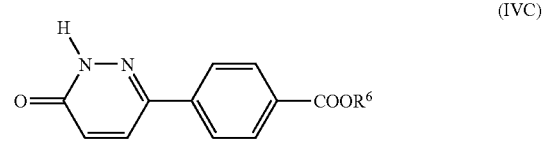

(IVC)

where $R^6$ is as defined above, with a compound of formula (A)

$R^2$-Z'''            (A)

where $R^2$ is as defined in relation to formula (I) and Z''' is a displaceable group such as halogen or sulphonate. The reaction suitably is carried out in an organic solvent such as dimethylformamide, 1,4-dioxane, dimethylsulphoxide, 1-methyl-2-pyrrolidinone, tetrahydrofuran, toluene or dichloromethane at temperatures in the range of from −78° C. to 150° C. in the presence of a base such as an alkali or alkaline earth metal carbonate.

Compounds of formula (IV) can be prepared by forming a pyridazinone ring on a compound of formula (V),

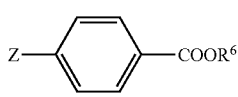
(V)

wherein Z is a functional group capable of cyclisation, using methods which are known in the literature.

For example, compounds of formula (IV) may be prepared by reacting a compound of formula (VI)

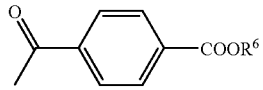
(VI)

wherein $R^6$ is as defined in relation to formula (IV), with a compound of formula (VII)

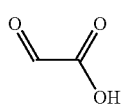
(VII)

and subsequently reacting the intermediate produced with a compound of formula (VIII)

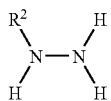
(VIII)

where $R^2$ is as defined in relation to formula (I).

The reaction of compounds of formula (VI) with (VII) can be carried out directly in the absence of solvent or in the presence of a solvent such as acetic acid, tetrahydrofuran, 1,4-dioxane, ethanol, or methanol. Suitably it is effected in the presence of a base such as an alkali metal carbonate or an alkali metal hydroxide, for example potassium carbonate or potassium hydroxide. Temperatures in the range of from −20° C. to 200° C. may be employed, and any heating may be conveniently carried out using microwave heating.

For the subsequent reaction of the product with the compound of formula (VIII), suitable reaction conditions include the optional use of an organic solvent such as dimethylsulphoxide, 1,4-dioxane, tetrahydrofuran, acetonitrile or water. Temperatures in the range from 0° C. to 200° C. can be used, and conveniently, the reaction is effected at the reflux temperature of the solvent.

Compounds of formula (VIII) are known compounds or can be prepared from known compounds using conventional methods.

Alternatively, a compound of formula (I) may be prepared by reaction of a compound of the formula (IX):

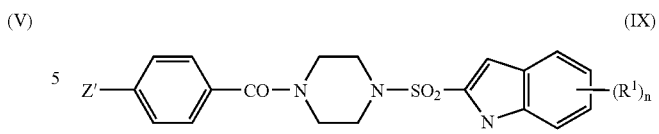
(IX)

wherein Z' is a displaceable group such as halo, with a compound of formula (X)

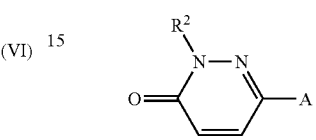
(X)

wherein $R^2$ is as defined in relation to formula (I) and A is an activating group. Suitable activating groups A include metalised derivatives, such as with zinc or tin, and borane derivatives. The compound of formula (X) is reacted with a compound of the formula (IX) to effect cross coupling where Z is triflate or a halo group, such as iodo, bromo or chloro. Suitably the reaction is catalysed by use of a transition state metal catalyst, such as palladium, for example $Pd(PPh_3)_4$.

Alternatively it is possible that the compound of formula (X) contains the displaceable group Z and the phenyl ring is activated with the group A, and the reaction performed as described above.

Compounds of formula (X) are either known compounds or they can be prepared by conventional methods, for example, by alkylation of compounds of formula compounds of formula (Xa)

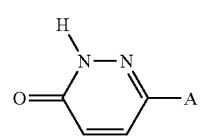
(Xa)

In yet another alternative, compounds of formula (I) can be prepared by forming an appropriately substituted pyridazinone ring on compounds of formula (IX), wherein Z' is a functional group capable of cyclisation. Suitable reagents and conditions are described above in relation to the reaction between compounds (VI), (VII) and (VIII).

Compounds of formula (I) may also be prepared by reacting a compound of the formula (XI):

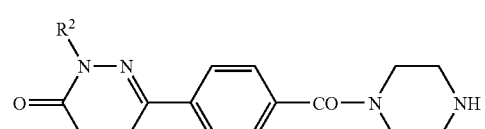
(XI)

where $R^2$ is as defined in relation to formula (I), with a compound of the formula (XII):

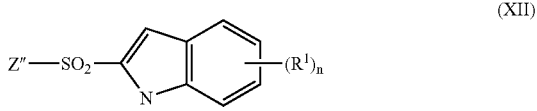

(XII)

wherein Z" is a displaceable group for example chloro, under conditions similar to those described above for the reaction between compounds of formula (II) and (III).

In addition, compounds of formula (I) may be prepared by reacting a compound of formula (XIII)

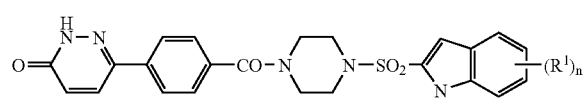

(XIII)

wherein $R^1$ and n are as defined in relation to formula (I), and the indole ring is optionally protected, with a compound of formula (A) as defined above, and thereafter if necessary, removing any indole protecting groups. Again reaction conditions are similar to those described above in relation to the reaction of the compound of formula (A) with a compound of formula (IVC).

Compounds of formula (XIII) can be prepared by methods described in see WO 99/57113. In particular, these methods are analogous to those described above, for the reaction of compound (II) with a compound of formula (III), but in this case the compound of formula (III) will be 4-(3-1H-pyrazin-6-onyl)-benzoic acid, which can be prepared by the method described by: Coates, W. J.; McKillop, A., *Synthesis*, 1993, 334-342.

When a pharmaceutically-acceptable salt of a compound of the formula (I) is required, it may be obtained, for example, by reaction of said compound with a suitable acid or base using a conventional procedure.

When an optically active form of a compound of the formula (I) is required, it may be obtained, for example, by carrying out one of the aforesaid procedures using an optically active starting material or by resolution of a racemic form of said compound using a conventional procedure, for example by the formation of diastereomeric salts, use of chromatographic techniques, conversion using stereospecific enzymatic processes, or by addition of temporary extra chiral group to aid separation.

As stated previously, the compounds of the formula (I) are inhibitors of the enzyme Factor Xa. The effects of this inhibition may be demonstrated using one or more of the standard procedures set out hereinafter:

a) Measurement of Factor Xa Inhibition

The FXa inhibitor potency was measured with a chromogenic substrate method, in a Plato 3300 robotic microplate processor (Rosys AG, CH-8634 Hombrechtikon, Switzerland), using 96-well, half-volume microtiter plates (Costar, Cambridge, Mass., USA; Cat No 3690). Stock solutions of test substance in DMSO (72 µL), 10 mmol/L, alternatively 1 mmol/L were diluted serially 1:3 (24+48 µL) with DMSO to obtain ten different concentrations, which were analyzed as samples in the assay, together with controls and blanks. As control sample melagatran was analysed. The dilutions of each test substance were analyzed consecutively, row-wise on the microtiter plate, with wash-cycles between substances to avoid cross-contamination. First 2 µL of test sample or DMSO for the blank were added, followed by 124 µL of assay buffer (0.05 mol/L Tris-HCl pH 7.4 at 37° C., 5 mM $CaCl_2$, ionic strength 0.15 adjusted with NaCl, 0.1% bovine serum albumin, ICN Biomedicals, Inc, USA, 1 g/L) and 12 µL of chromogenic substrate solution (S-2765, Chromogenix, Mölndal, Sweden) and finally 12 µL of FXa solution (human FXa, Haematologic Technologies Inc., Essec Junction, Vt., USA), in buffer, was added, and the samples were mixed. The final assay concentrations were: test substance 0.0068-133, respectively 0.00068-13.3 µmol/L, S-2765 0.40 mmol/L ($K_M$=0.25 mmol/L) and FXa 0.1 nmol/L. The linear absorbance increase at 405 nm during 40 min incubation at 37° C. was used for calculation of percent inhibition for the test samples, as compared to references without inhibitor and/or enzyme. The $IC_{50}$-value, corresponding to the inhibitor concentration, which caused 50% inhibition of the FXa activity, was calculated by fitting the data to a three-parameter equation by Microsoft XLfit.

b) Measurement of Thrombin Inhibition

The thrombin inhibitor potency was measured with a chromogenic substrate method developed in-house in principle as described in a) for FXa but using instead 0.3 mM of the chromogenic substrate solution S-2366 (Chromogenix, Mölndal, Sweden) and 0.1 nmol/L human thrombin (Haematologic Technologies Inc., Essec Junction, Vt., USA).

c) Measurement of Anticoagulant Activity

An in vitro assay whereby human blood is collected and added directly to a sodium citrate solution (3.2 g/100 mL, 9 parts blood to 1 part citrate solution). Plasma is prepared by centrifugation (1000 g, 15 minutes) and stored at −80° C.) and an aliquot was rapidly thawed at 37° C. on the day of the experiment and kept on ice before addition to the coagulometer cups. Conventional prothrombin time (PT) tests are carried out in the presence of various concentrations of a test compound and the concentration of test compound required to double the clotting time is determined. Thromborel® S (Dade Behring, Liederbach, Germany) was reconstituted with 10 mL water. This solution was kept at 4° C. and was used within one week. Before the experiment the solution was kept at 37° C. for at least 30 minutes before start of the experiment. A ball coagulation timer KC 10A from Heinrich Amelung GmbH. (Lemgo, Germany) was used to study if the compounds could prevent coagulation in human plasma. The time for 50 µl plasma with compound to coagulate after addition of 100 µl Thromborel S, the Prothrombin Time or $PT_i$, is compared with the time it takes for pure plasma to coagulate, $PT_0$. With this technique the change in viscosity in the stirred solution is used to define clotting. The IC50 is calculated from the curve of $PT_i/PT_o$ versus the inhibitor concentration in plasma, id est three times the final assay concentration.

d) An in vivo Measurement of Antithrombotic Activity

The abdoman is opened and the caval vein exposed. The thrombotic stimulus is partial stasis to the caval vein and a piece of filter paper soaked with ferric chloride and superimposed to the external surface of the vein. Thrombus size is determined as the thrombus wet weight at the end of the experiment. (Ref Thromb. Res. 2002; 107:163-168).

When tested in the above mentioned screen a) Measurement of Factor Xa Inhibition, the compounds of the Examples gave IC50 values for inhibition of Factor Xa activity of less than 10 µM, indicating that the compounds of the invention are expected to possess useful therapeutic properties.

Specimen results are shown in the following Table:

| Compound | IC$_{50}$ value (nM) |
|---|---|
| Example 3 | 55 |
| Example 9 | 38 |

A feature of the invention is a compound of formula (I), or a pharmaceutically acceptable salt thereof, for use in medical therapy.

According to a further feature of the invention there is provided a pharmaceutical composition which comprises a heterocyclic derivative of formula (I), or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a heterocyclic derivative of the formula (I), or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocyclic derivative of formula (I), or a pharmaceutically-acceptable salt thereof, for use in a method of treatment of the human or animal body by therapy.

The invention also includes the use of such an active ingredient in the production of a medicament for use in:
(i) producing a Factor Xa inhibitory effect;
(ii) producing an anticoagulant effect;
(iii) producing an antithrombotic effect;
(iv) treating a Factor Xa mediated disease or medical condition;
(v) treating a thrombosis mediated disease or medical condition;
(vi) treating coagulation disorders; and/or
(vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of the formula (I) will naturally vary according to the nature and severity of the medical condition, the age and sex of the animal or patient being treated and the route of administration, according to well known principles of medicine. As mentioned above, compounds of the formula (I) are useful in the treatment or prevention of a variety of medical disorders where anticoagulant therapy is indicated. In using a compound of the formula (I) for such a purpose, it will generally be administered so that a daily oral dose in the range, for example, 0.5 to 100 mg/kg body weight/day is received, given if required in divided doses. In general lower doses will be administered when a parenteral route is employed, for example a dose for intravenous administration in the range, for example, 0.01 to 10 mg/kg body weight/day will generally be used. For preferred and especially preferred compounds of the invention, in general, lower doses will be employed, for example a daily dose in the range, for example, 0.1 to 10 mg/kg body weight/day. In general a preferred dose range for either oral or parenteral administration would be 0.01 to 10 mg/kg body weight/day.

Although the compounds of formula (I) are primarily of value as therapeutic or prophylactic agents for use in warm-blooded animals including man, they are also useful whenever it is required to produce an anticoagulant effect, for example during the ex-vivo storage of whole blood or in the development of biological tests for compounds having anticoagulant properties.

The compounds of the invention may be administered as a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known anti-hypertensive agent.

The invention will now be illustrated in the following Examples in which, unless otherwise stated:—
(i) Yields are given for illustration only and are not necessarily the maximum attainable;
(ii) The end-products have satisfactory high resolution mass spectral (HRMS) data as analysed on a Micromass LCT system equipped with a TOF mass spectrometer. MS conditions: Electrospray ionization, positive mode, capillary voltage 2.3 kV and desolvation temperature 150° C. Accurate mass was determined for positive ionization using leucine enkephaline (m/z 556.2771) as lock mass. Structure were confirmed by nuclear magnetic resonance (NMR). Chemical shift values were measured on the delta scale; the following abbreviations have been used: s, singlet; d, doublet; t, triplet; q, quartet; m, multiplet;
(iii) Intermediates were generally characterised as the end products with the exception of HRMS data.
(ii). Purity was assessed by, high performance liquid chromatography instruments equipped with UV detectors operating at 254 nm and by NMR.
(iv) Purification of intermediates and products were done by flash chromatography or high performance reversed phase preparative liquid chromatography (HPLC).

EXAMPLE 1

6-{4-[4-(5-Chloro-1H-indole-2-sulphonyl)-piperazine-1-carbonyl]-phenyl}-2-methyl-2H-pyridazin-3-one Step A 4-Acetylbenzoic acid (5.00 gram, 30.5 mmol) and 3.19 gram of glyoxalic acid monohydrate (34.7 mmol, 1.14 eq.) were stirred in 50 mL of acetic acid at 110° C. for 20 hours, and then cooled to 40° C. Solvent was removed with evaporator in vacuo. To the residue was added water (15 mL), and the mixture cooled with an ice bath. The resulting solution was titrated with ammonia solution until pH 9. Methyl hydrazine (3.00 mL 57.3 mmol, 1.88 eq.) was added, and the mixture was heated to reflux for 5 hours. The solution was concentrated in vacuo. To the solid residue was added 1 M cold aqueous hydrochloric acid until the solution had a pH 1~2. The solid was filtrated and dried in vacuo over night. The solids were treated with diethyl ether (200 mL) and the mixture was ultrasonicated at room temperature for 3 hours and filtered. The solids were treated with 200 mL of diethyl ether and stirred for 2 hours before filtration, which after drying gave 4-(1-methyl-6-oxo-1,6-dihydro-pyridazin-3-yl)-benzoic acid in 33% isolated yield.

$^1$H NMR (300 MHz; N,N-dimethylformamide-d$_7$ as solvent and internal reference) δ(ppm) 3.81 (s, 3H), 7.06 (d, 1H, J=9.7 Hz), 8.04-8.16 (m, 5H).

Step B

To a solution of 4-(1-methyl-6-oxo-1,6-dihydro-pyridazin-3-yl)-benzoic acid, (0.637 g, 2.76 mmol) in N,N-dimethylformamide was added 1,1'-carbonyldiimidazole (0.930 g, 5.74 mmol, 2.07 eq.). The resulting solution was stirred at room temperature for 5 hours, whereupon 5-chloro-2-(piperazin-1-ylsulphonyl)-1H-indole (see WO 99/57113, 0.622 g, 2.08 mmol, 1.11 eq.) was added. The reaction mixture was stirred at 25° C. for 14 h and then evaporated in vacuo. The residue was purified by flash column chromatography: first eluting with ethyl acetate:toluene (2:1), then with ethyl acetate. During concentration of the desired fraction, a white solid precipitated. The solid was triturated with hot ethyl acetate (50 mL) to remove a trace of impurity. After drying, pale yellow solid were isolated. De-colorization on charcoal using hot methanol together with the re-crystallization in methanol, gave 0.79 gram 6-{4-[4-(5-chloro-1H-indole-2-sulphonyl)-piperazine-1-carbonyl]-phenyl}-2-methyl-2H-pyridazin-3-one as fine white crystals (yield 56%).

$^1$H NMR (500 MHz; N,N-dimethylformamide-d$_7$ as solvent and internal reference) δ(ppm) 3.23 (m, 4H), 3.50-3.90 (m, 4H), 3.78 (s, 3H), 7.03 (d, 1H, J=9.6 Hz), 7.10 (m, 1H), 7.36-7.38 (m, 1H), 7.52 (m, 2H), 7.59 (m, 1H), 7.83 (m, 1H), 7.95 (m, 2H), 8.10 (d, 1H, J=9.6 Hz).

HRMS (ESI+) calc. [M+H]$^+$ 510.1003, found 510.1025.

EXAMPLE 2

6-{4-[4-(5-Chloro-1H-indole-2-sulphonyl)-piperazine-1-carbonyl]-phenyl}-2-(2-dimethylamino-ethyl)-2H-pyridazin-3-one Step A To a microwave vial was added 3,6-dichloropyridazine (645 mg, 4.33 mmol), potassium acetate (425 mg, 4.33 mmol) and 9 mL acetic acid/water (5:1). The reaction mixture was heated at 140° C. for 70 minutes. The solvent was evaporated and the crude was purified by preparative HPLC using a gradient of acetonitrile/5% acetonitrile-water phase containing 0.1 M ammonium acetate, to give 436 mg of 6-chloro-2H-pyridazin-3-one (77% yield).

$^1$H NMR (400 MHz; methanol-d$_4$ as solvent and internal reference) δ(ppm) 6.96 (d, 1H), 7.45 (d, 1H).

Step B

To a solution of 6-chloro-2H-pyridazin-3-one (500 mg, 3.83 mmol) in 5 mL dimethylformamide was added 2-dimethylaminoethyl chloride hydrochloride (828 mg, 5.75 mmol), potassium carbonate (1.59 g, 11.5 mmol) and sodium iodide (632 mg, 4.21 mmol). The mixture was stirred over night at 65° C. Solvent was evaporated. The crude product was dissolved in water and purified by preparative HPLC using a gradient of acetonitrile/5% acetonitrile—water phase containing 0.1 M ammonium acetate, to give 174 mg of 6-chloro-2-(2-dimethylamino-ethyl)-2H-pyridazin-3-one as light brown crystals after freeze drying (22% yield).

$^1$H NMR (400 MHz; methanol-d$_4$ as solvent and internal reference) δ(ppm) 2.35 (s, 6H), 2.82 (t, 2H), 4.26 (t, 2H), 6.98 (d, 1H), 7.43 (d, 1H).

Step C

5-Chloro-2-(piperazin-1-ylsulphonyl)-1H-indole (5.42 g, 18.1 mmol) was added to a solution of 4-carboxyphenyl boronic acid (3.00 g, 18.1 mmol) N,N-diisopropylethylamine (2.34 g, 18.1 mmol) and O-(benzotriazol-1-yl)-N,N,N',N'-tetramethyluronium tetrafluoroborate (5.81 g, 18.1 mmol) in 80 mL N,N-dimethylformamide, the mixture was stirred for 2 hours at room temperature. N,N-Dimethylformamide was removed in vacuo and the crude was purified by flash chromatography three times (dichloromethane/methanol, 100-98/2) to give 4-({4-[(5-chloro-1H-indol-2-yl)sulphonyl]piperazin-1-yl}carbonyl)phenyl boronic acid as a colourless solid (56% yield).

$^1$H NMR (400 MHz; methanol-d$_4$ as solvent and internal reference) δ(ppm) 3.04-3.24 (m, 4H), 3.46-3.92 (m, 4H), 6.99-7.00 (m, 1H), 7.27-7.32 (m, 3H), 7.45 (d, 1H), 7.61-7.65 (m, 2H), 7.68-7.70 (m, 1H).

Step D

6-Chloro-2-(2-dimethylamino-ethyl)-2H-pyridazin-3-one (76 mg, 0.38 mmol), cesium carbonate (122 mg, 0.38 mmol) and bis(triphenylphosphine)palladium II chloride (21.9 mg, 0.03 mmol) was added to a microwave vial. The vial was evacuated and filled with argon twice. 4-({4-[(5-Chloro-1H-indol-2-yl)sulphonyl]piperazin-1-yl}carbonyl)phenyl boronic acid (140 mg, 0.31 mmol) dissolved in 4 mL 1,2-dimethoxyethane/water/ethanol (7:3:2) was added and the vial was once again evacuated and filled with argon. The reaction mixture was heated at 150° C. for 100 seconds, filtrated and purified by preparative HPLC using a gradient of acetonitrile/5% acetonitrile-water phase containing 0.1M ammonium acetate, to give 107 mg of 6-{4-[4-(5-chloro-1H-indole-2-sulphonyl)-piperazine-1-carbonyl]-phenyl}-2-(2-dimethylamino-ethyl)-2H-pyridazin-3-one after evaporation and freeze drying over night (60% yield).

$^1$H NMR (400 MHz; methanol-d$_4$ as solvent and internal reference) δ(ppm) 2.40 (s, 6H), 2.94 (t, 2H), 3.08-3.24 (m, 4H), 3.48-3.91 (m, 4H), 4.42 (t, 2H), 7.00-7.01 (m, 1H), 7.07 (d, 1H), 7.27-7.31 (m, 1H), 7.43-7.48 (m, 3H), 7.69-7.70 (m, 1H), 7.93-8.01 (m, 3H).

HRMS (ESI+) calc. [M+H]$^+$ 569.1738, found 569.1758.

EXAMPLE 3

6-{4-[4-(5-Chloro-1H-indole-2-sulphonyl)-piperazine-1-carbonyl]-phenyl}-2-(2-methylamino-ethyl)-2H-pyridazin-3-one The compound was prepared according to the procedure for Example 2 in 26% isolated yield from 4-({4-[(5-chloro-1H-indol-2-yl)sulphonyl]piperazin-1-yl}carbonyl)-phenyl boronic acid.

$^1$H NMR (400 MHz; methanol-d$_4$ as solvent and internal reference) δ (ppm) 2.72 (s, 3H), 3.05-3.26 (m, 4H), 3.49 (t, 2H), 3.53-3.95 (m, 4H), 4.56 (t, 2H), 7.00-7.01 (m, 1H), 7.13 (d, 1H), 7.28-7.31 (m, 1H), 7.44-7.49 (m, 3H), 7.68-7.71 (m, 1H), 7.96 (d, 2H), 8.06 (d, 1H).

HRMS (ESI+) calc. [M+H]$^+$ 555.1581, found 555.1559.

EXAMPLE 4

6-{4-[4-(5-Chloro-1H-indole-2-sulphonyl)-piperazine-1-carbonyl]-phenyl}-2-ethyl-2H-pyridazin-3-one The compound was prepared according to the procedure for Example 1 in 29% isolated yield.

$^1$H NMR (400 MHz; N,N-dimethylformamide-d$_7$ as solvent and internal reference) δ(ppm) 1.36 (t, 3H), 3.16-3.28 (m, 4H), 3.50-3.90 (m, 4H), 4.22 (q, 2H), 7.04 (d, 1H, J=9.9 Hz), 7.10 (m, 1H), 7.35-7.38 (m, 1H), 7.52 (m, 2H), 7.59 (m, 1H), 7.83 (m, 1H), 7.97 (m, 2H), 8.09 (d, 1H, J=9.9 Hz).

HRMS (ESI+) calc. [M+H]$^+$ 526.1316, found. 526.1298

EXAMPLE 5

2-Butyl-6-{4-[4-(5-chloro-1H-indole-2-sulphonyl)-piperazine-1-carbonyl]-phenyl}-2H-pyridazin-3-one The compound was prepared according to the procedure for Example 1 in 15% isolated yield.

$^1$H NMR (400 MHz; N,N-dimethylformamide-d$_7$ as solvent and internal reference) δ(ppm) 0.93 (t, 3H), 1.36 (m, 2H), 1.79 (m, 2H), 3.10-3.90 (m, 8H), 4.20 (t, 2H), 7.04 (d, 1H, J=9.7 Hz), 7.10 (m, 1H), 7.35-7.38 (m, 1H), 7.52 (m, 2H), 7.59 (m, 1H), 7.83 (m, 1H), 7.97 (m, 2H), 8.09 (d, 1H, J=9.7 Hz).

HRMS (ESI+) calc. [M+H]$^+$ 554.1628, found. 554.1629

EXAMPLE 6

6-{4-[4-(5-Chloro-1H-indole-2-sulphonyl)-piperazine-1-carbonyl]-phenyl}-2-(2-hydroxy-ethyl)-2H-pyridazin-3-one The compound was prepared according to the procedure for Example 9 in 40% isolated yield.

$^1$H-NMR (400 MHz; dimethyl sulphoxide-d$_6$ as solvent and internal reference) δ(ppm) 2.90-3.85 (m, 8H), 3.77 (t, 2H), 4.20 (t, 2H), 4.82 (m, 1H), 7.02 (m, 1H), 7.04 (d, 1H, J=9.7 Hz), 7.32 (m, 1H), 7.45-7.51 (m, 3H), 7.78 (m, 1H), 7.90 (m, 2H), 8.04 (d, 1H, J=9.7 Hz).

HRMS (ESI+) calc. [M+H]$^+$ 542.1265, found. 542.1220

EXAMPLE 7

6-{4-[4-(5-Chloro-1H-indole-2-sulphonyl)-piperazine-1-carbonyl]-phenyl}-2-(2,2,2-trifluoro-ethyl)-2H-pyridazin-3-one The compound was prepared according to the procedure for Example 1 in 19% isolated yield.

$^1$H NMR (400 MHz; N,N-dimethylformamide-d$_7$ as solvent and internal reference) δ(ppm) 3.12-3.34 (m, 4H), 3.50-3.80 (m, 4H), 5.10 (q, 2H), 7.11 (m, 1H), 7.20 (d, 1H, J=9.8 Hz), 7.34-7.37 (m, 1H), 7.53 (m, 2H), 7.61 (m, 1H), 7.83 (m, 1H), 7.97 (m, 2H), 8.18 (d, 1H, J=9.8 Hz).

HRMS (ESI+) calc. [M+H]$^+$ 580.1033, found 580.1009.

EXAMPLE 8

6-{4-[4-(5-Chloro-1H-indole-2-sulphonyl)-piperazine-1-carbonyl]-phenyl}-2-(2-methoxy-ethyl)-2H-pyridazin-3-one The compound was prepared according to the procedure for Example 9 in 35% isolated yield.

$^1$H-NMR (400 MHz; dimethyl sulphoxide-d6 as solvent and internal reference) δ(ppm) 2.96-3.26 (m, 4H), 3.25 (s, 3H), 3.30-3.80 (m, 4H), 3.75 (t, 2H), 4.31 (t, 2H), 7.03 (m, 1H), 7.05 (d, 1H, J=9.7 Hz), 7.33 (m, 1H), 7.46-7.51 (m, 3H), 7.79 (m, 1H), 7.90 (m, 2H), 8.04 (d, 1H, J=9.7 Hz).

HRMS (ESI+) calc. [M+H]$^+$ 556.1422, found. 556.1385

EXAMPLE 9

6-{4-[4-(5-Chloro-1H-indole-2-sulphonyl)-piperazine-1-carbonyl]-phenyl}-2-[2-(2-methoxy-ethoxy)-ethyl]-2H-pyridazin-3-one 6-[4-({4-[(5-Chloro-1H-indol-2-yl)sulphonyl]piperazin-1-yl}carbonyl)phenyl]-pyridazin-3-ol (see WO 99/57113, 0.054 gram, 0.11 mmol), 0.016 gram of anhydrous potassium carbonate (0.11 mmol, 1.0 eq.) and 0.02 gram of 1-bromo-2-(2-methoxy-ethoxy)ethane (0.11 mmol, 1.0 eq.) were mixed in 1.5 mL of dry N,N-dimethylform-amide. The mixture was treated with microwave at 150° C. for 1 hour. Without any work-up, purification was performed on preparative HPLC, which gave 0.023 gram of 6-{4-[4-(5-chloro-1H-indole-2-sulphonyl)-piperazine-1-carbonyl]-phenyl}-2-[2-(2-methoxy-ethoxy)-ethyl]-2H-pyridazin-3-one (yield 36%).

$^1$H-NMR (400 MHz; dimethyl sulphoxide-d6 as solvent and internal reference) δ(ppm) 2.96-3.26 (m, 4H), 3.16 (s, 3H), 3.38 (m, 2H), 3.30-3.80 (m, 4H), 3.53 (m, 2H), 3.82 (t, 3H), 4.30 (t, 3H), 7.03 (m, 1H), 7.06 (d, 1H, J=9.7 Hz), 7.33 (m, 1H), 7.45-7.51 (m, 3H), 7.79 (m, 1H), 7.91 (m, 2H), 8.04 (d, 1H, J=9.7 Hz).

HRMS (ESI+) calc. [M+H]$^+$ 600.1683, found. 600.1671

EXAMPLE 10

6-{4-[4-(5-Chloro-1H-indole-2-sulfonyl)-piperazine-1-carbonyl]-phenyl}-2-fluoromethyl-2H-pyridazin-3-one Step A 6-Chloro-pyridazin-3-ol (460 mg, 3.52 mmol) was dissolved in 3 mL 1,4-dioxane. Potassium carbonate was added to the solution (1.0 g, 7.2 mmol), followed by 1 mL dimethylformamide. The mixture was sealed in a microwave vial. Cooled down to −30° C., the vial was fed with bromofluoromethane ( 0.74 g, 1.86 mmol), which liquefied at the low temperature in the vial. The vial was allowed to reach room temperature and subsequently heated at 150° C. for 10 minutes. After cooling the reaction mixture was filtered and the solution was purified by preparative reversed phase HPLC. After pooling of fractions and removal of organic solvents in vacuo, the remaining acqueous phase was extracted with dichloromethane. The organic layers were combined and concentrated in vacou whereupon the product precipitated. After filtration and drying of the solids in vacuo, 173 mg was isolated (30% yield).

$^1$H NMR (400 MHz, CDCl$_3$ as solvent and internal reference) δ(ppm) 5.97 (d, 2H, J=51 Hz), 6.95 (d, 1H, J=10 Hz), 7.22 (d, 1H, J=10 Hz).

Step B

To a solution of 4-(dihydroxyboryl)benzoic acid (1.08 g, 6.51 mmol) in 8 mL dimethylformamide was added diisopropylethylamine (0.88 g, 6.8 mmol) and O-(benzotriazol-1-yl)-N,N,N',N'-tetramethyluronium tetrafluoroborate (2.19 g, 6.83 mmol). The mixture was stirred until it became homogenous whereafter 5-chloro-2-(piperazine-1-sulfonyl)-1H-indole (1.85 g, 6.18 mmol) in 8 mL dimethylformamide was added. The mixture was stirred 15 hour at room temperature. The crude reaction mixture was purified by preparative HPLC. Freeze drying of pooled fractions gave 2.23 g product (77% yield).

$^1$H NMR (400 MHz; N,N-dimethylformamide-$d_7$ as solvent and internal reference) δ(ppm) 3.21 (m, 4H), 3.68 (m, 4H), 7.11 (s, 1H), 7.29-7.38 (m, 3H), 7.61 (m, 2H), 7.83 (m, 1H), 7.92 (m, 2H), 8.46 (broad, s, 2H).

Step C

6-Chloro-2-fluoromethyl-2H-pyridazin-3-one (85 mg, 0.52 mmol), [4-({4-[(5-chloro-1H-indol-2-yl)sulfonyl]piperazin-1-yl}carbonyl)phenyl]boronic acid (236 mg, 0.53 mmol), cesium carbonate (209 mg, 0.64 mmol), bis(triphenylphosphine) palladium II chloride (26 mg, 0.04 mmol) and 2.2 mL 1,2-dimethoxyethane/water/ethanol (7:3:2) were added to a microwave tube. The reaction mixture was heated at 150° C. for 150 seconds. The crude reaction mixture was purified by preparative HPLC. After freeze drying of pooled fractions, 106 mg product was obtained as a white powder (38% yield).

$^1$H NMR (400 MHz; N,N-dimethylformamide-$d_7$ as solvent and internal reference) δ(ppm) 3.22 (m, 4H), 3.33-3.90 (m, 4H), 6.19 (d, 2H, J=52 Hz), 7.10 (s, 1H), 7.18 (m, 2H), 7.37 (m, 1H), 7.54-7.61 (m, 3H), 7.84 (s, 1H), 8.00 (m, 2H), 8.20 (m, 1H).

HRMS (ESI+) calc. [M+H]$^+$ 530.1065, found. 530.1067.

EXAMPLE 11

6-{4-[4-(5-Chloro-1H-indole-2-sulfonyl)-piperazine-1-carbonyl]-phenyl}-2-difluoromethyl-2H-pyridazin-3-one Step A 6-Chloro-pyridazin-3-ol (500 mg, 3.83 mmol) was dissolved in 3.5 mL dimethylformamide in a microwave vial. Potassium carbonate (2.12 g, 15.3 mmol), was added to the solution followed by microwave heating for 10 seconds at 100° C. The vial was cooled to −78° C., and thereafter fed with chlorodifluoromethane (3.68 g, 28.1 mmol). After warming to room temperature, the vial was heated to 60° C. in a microwave for 10 seconds, then gradually up to 130° C. while keeping the pressure below 22 bar (total reaction time 12 minutes). After filtration, the crude reaction mixture was purified by preparative HPLC. After pooling of fractions and removal of organic solvents in vacuo, the remaining acqueous phase was extracted with dichloromethane. The organic layers were combined and removal of solvents in vacou gave 158 mg of an slightly brown oily residue (23% yield).

$^1$H NMR (400 MHz, CDCl$_3$ as solvent and internal reference) δ(ppm) 7.14 (d, 1H, J=9.2 Hz), 7.56 (d, 1H, J=9.1 Hz), 7.63 (t, 1H, J=71.5 Hz).

Step B

6-Chloro-2-difluoromethyl-2H-pyridazin-3-one (94 mg, 0.52 mmol), [4-({4-[(5-chloro-1H-indol-2-yl)sulfonyl]piperazin-1-yl}carbonyl)phenyl]boronic acid (266 mg, 0.59 mmol), cesium carbonate (204 mg, 0.62 mmol), bis(triphenylphosphine) palladium II chloride (33 mg, 0.05 mmol) and 1.8 mL 1,2-dimethoxyethane/water/ethanol (7:3:2) were added to a microwave tube. The reaction mixture was heated at 150° C. for 150 seconds. The crude reaction mixture was purified by preparative HPLC. After freeze drying of pooled fractions, 190 mg product was obtained as a white powder (67% yield).

$^1$H NMR (400 MHz; N,N-dimethylformamide-$d_7$ and one drop of deuterium oxide as solvents, N,N-dimethylformamide-$d_7$ as internal reference) δ(ppm) 3.25 (m, 4H), 3.50-3.90 (m, 4H), 7.11 (s, 1H), 7.36-7.38 (m, 1H), 7.58-7.61 (m, 3H), 7.66 (m, 1H), 7.83 (m, 1H), 8.20 (m, 2H), 8.48 (m, 1H).

HRMS (ESI+) calc. [M+H]$^+$ 548.0971, found 548.0970.

EXAMPLE 12

6-{4-[4-(5-Chloro-1H-indole-2-sulfonyl)-2-oxo-piperazin-1-ylmethyl]-phenyl}-2-(2-morpholin-4-yl-ethyl)-2H-pyridazin-3-one Step A 6-Chloro-pyridazin-3-ol (5.34 g, 40.8 mmol), 4-(2-chloro-ethyl)-morpholine hydrochloride (7.61 g, 40.8 mmol) and potassium carbonate (11.3 g, 81.7 mmol) were added to 20 mL of acetonitrile, 10 mL of N,N-dimethylformamide and 0.5 mL of water. The reaction mixture was heated using an oil bath at 116° C. After 4 hours, LC/MS showed the disappearance of 6-chloro-pyridazin-3-ol and the formation of the alkylated product. After cooling to room temperature, 100 mL of water was added to the mixture. The aqueous phase was extracted twice with ethyl acetate. The combined organic layers were dried over Na$_2$SO$_4$, concentrated, and subjected to flash column chromatography (ethyl acetate/hexane/triethyl amine; 1:6:0.05) on silica gel to give 6-chloro-2-(2-morpholin-4-yl-ethyl)-2H-pyridazin-3-one after removal of solvents in vacuo. To the residue was added 20 mL of 4 M aqueous HCl and 20 mL of methanol were added (pH ~2). The mixture was concentrated to get a solid residue, which could be further purified through re-crystallisation in hot ethanol. Finally, 4.2 g (37%) of the product as a mono hydrochloride salt was obtained as colourless solid material.

$^1$H NMR (400 MHz; CD$_3$OD as solvent and internal reference) δ (ppm) 3.24 (m, 2H), 3.64 (t, 3H, J=5.8 Hz), 3.68 (m, 2H), 3.83 (m, 2H), 4.07 (m, 2H), 4.55 (t, 3H, J=5.8 Hz), 7.06 (d, 1H, J=9.8 Hz), 7.56 (d, 1H, J=9.8 Hz).

Step B

6-Chloro-2-(2-morpholin-4-yl-ethyl)-2H-pyridazin-3-one hydrochloride, (63 mg, 0.22 mmol), 4-({4-[(5-chloro-1H-indol-2-yl)sulphonyl]piperazin-1-yl}carbonyl)-phenyl boronic acid (78 mg, 0.17 mmol), caesium carbonate (156 mg, 0.48 mmol), and bis(triphenylphosphine) palladium (II) chloride (11 mg, 0.02 mmol,) were mixed in 2.0 mL of dimethyl acetamide/water/ethanol; 7:3:2) in a microwave vial. The reaction was heated to 150° C. for 150 seconds. After cooling, the mixture was filtered and loaded onto a reversed-phase preparative HPLC for purification. After freezing dry of pooled fractions, 71 mg (67%) of the product was obtained as a white powder.

$^1$H NMR (400 MHz; N,N-dimethylformamide-$d_7$ as solvent and internal reference) δ (ppm) 2.48 (m, 2H), 2.77 (m, 2H), 3.30-3.60 (m, 10H), 3.94 (s, 2H), 4.33 (t, 2H, J=6.7 Hz), 4.62 (s, 2H), 7.03 (d, 1H, J=9.6 Hz), 7.18 (s, 1H), 7.29 (m, 2H), 7.35-7.38 (m, 1H), 7.59 (m, 1H), 7.78 (m, 2H), 7.84 (m, 1H), 8.01 (d, 1H, J=9.6 Hz).

HRMS (ESI+) [M+H]$^+$, calculated−found=−2.7 mDa.

The invention claimed is:

1. A compound of formula (I)

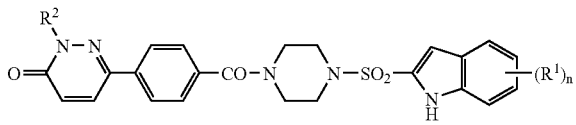

wherein R² is a group OR⁴ or a group —Y—R⁵ where
R⁴ is hydrogen or $C_{1-4}$alkyl,
Y is $C_{1-4}$alkylene,
R⁵ is halo, hydroxy, $C_{1-2}$alkoxy, $C_{1-2}$alkoxy$C_{1-2}$alkoxy $C_{1-4}$, or a group NR⁷R⁸ where R⁷ and R⁸ are independently selected from hydrogen, $C_{1-2}$alkyl, hydroxy$C_{1-2}$alkyl or alkoxy$C_{1-2}$alkyl, or R⁷ and R⁸ together with the nitrogen atom to which they are attached form a saturated 5-6-membered heterocyclic ring which optionally contains an additional heteroatom;
n is one or two and each R¹ is independently selected from halo, halo$C_{1-2}$alkyl, hydroxy, amino, $C_{1-2}$alkylamino or di-$C_{1-2}$dialkylamino;
or a pharmaceutically acceptable salt thereof.

2. The compound according to claim 1 wherein R² is a group —Y—R⁵.

3. The compound according to claim 2 wherein Y is a $C_{1-2}$alkylene group.

4. The compound according to claim 1 wherein R² is a group —Y—R⁵ and R⁵ is a group NR⁷R⁸ where R⁷ and R⁸ are independently selected from hydrogen, $C_{1-2}$alkyl, hydroxy$C_{1-2}$alkyl or alkoxy$C_{1-2}$alkyl, or R⁷ and R⁸ together with the nitrogen atom to which they are attached form a saturated 5-6-membered heterocyclic ring which optionally contains an additional heteroatoms.

5. The compound according to claim 1 wherein n is 1.

6. The compound according to claim 1 wherein at least one R¹ group is a halo group.

7. The compound according to claim 6 wherein R¹ is bromo or chloro.

8. The compound according to claim 1 wherein an R¹ group is present at a position equivalent to the 5-position as numbered on the indole ring.

9. The compound according to claim 1 which is
6-[4-({4-[(5-chloro-1H-indol-2-yl)sulphonyl]piperazin-1-yl}carbonyl)phenyl]-2-[2-(dimethylamino)ethyl]pyridazin-3(2H)-one,
6-{4-[4-(5-chloro-1H-indole-2-sulfonyl)-piperazine-1-carbonyl]-phenyl}-2-(2-methylaminoethyl)-2H-pyridazin-3-one,
6-{4-[4-(5-chloro-1H-indole-2-sulfonyl)-piperazine-1-carbonyl]-phenyl}-2-(2-hydroxyethyl)-2H-pyridazin-3-one,
6-{4-[4-(5-chloro-1H-indole-2-sulfonyl)-piperazine-1-carbonyl]-phenyl}-2-(2,2,2-trifluoroethyl)-2H-pyridazin-3-one,
6-{4-[4-(5-chloro-1H-indole-2-sulfonyl)-piperazine-1-carbonyl]-phenyl}-2-(2-methoxyethyl)-2H-pyridazin-3-one,
6-[4-({4-[(5-chloro-1H-indol-2-yl)sulphonyl]piperazin-1-yl}carbonyl)phenyl]-2-[2-(2-methoxyethoxy)ethyl]pyridazin-3(2H)-one,
6-{4-[4-(5-Chloro-1H-indole-2-sulfonyl)-piperazine-1-carbonyl]-phenyl}-2-fluoromethyl-2H-pyridazin-3-one,
6-{4-[4-(5-Chloro-1H-indole-2-sulfonyl)-piperazine-1-carbonyl]-phenyl}-2-difluoromethyl-2H-pyridazin-3-one or
6-{4-[4-(5-Chloro-1H-indole-2-sulfonyl)-2-oxo-piperazin-1-ylmethyl]-phenyl}-2-(2-morpholin-4-yl-ethyl)-2H-pyridazin-3-one.

10. A process for preparing a compound of formula (I) as defined in claim 1 which process comprises either
(a) reacting an amine of formula (II)

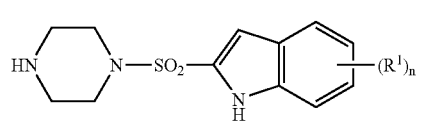

with an acid of the formula (III)

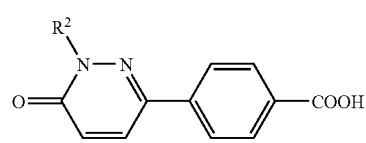

or a reactive derivative thereof; or
(b) reacting a compound of the formula (VIII):

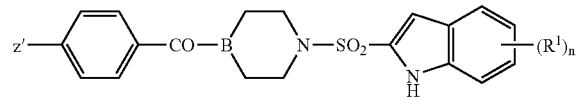

(VIII)
wherein Z' is a displaceable group, with a compound of formula (IX)

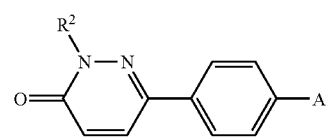

wherein R² is as defined claim 1 and A is an activating group, or
(c) forming a substituted pyridazinone ring on compounds of formula (VIII), wherein Z' is a functional group capable of cyclisation;
(d) by reacting a compound of the formula (X):

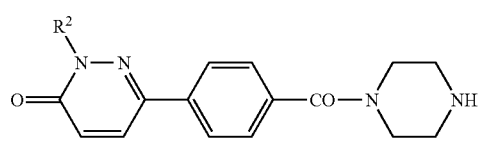

where R² is as defined in claim 1, with a compound of the formula (XI):

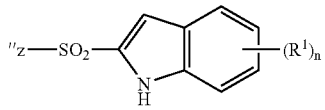

(XI)

wherein R¹ and n are as defined in claim 1 and Z″ is a displaceable group, under conditions similar to those described above in process (a); or (e) reacting a compound of formula (XIII)

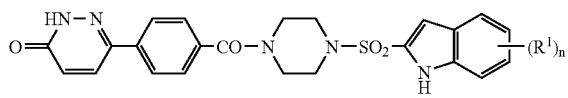

(XIII)

wherein R¹ and n are as defined claim 1, and the indole ring is optionally protected, with a compound of formula (A)

$$R^2-Z'''$$ (A)

where R² is as defined in claim 1 and Z''' is a displaceable group, and thereafter optionally removing any indole protecting groups.

11. A pharmaceutical composition comprising a compound of formula (I), or a pharmaceutically-acceptable salt thereof, as defined in claim 1 or claim 9, with a pharmaceutically-acceptable diluent or carrier.

12. A method for producing an antithrombotic or anticoagulant effect in a warm-blooded animal in need thereof comprising administering an effective amount of a compound of formula (I), as defined in claim 1 or claim 9, or a pharmaceutically-acceptable salt thereof.

\* \* \* \* \*